United States Patent [19]

Brown et al.

[11] Patent Number: 4,521,418

[45] Date of Patent: Jun. 4, 1985

[54] GUANIDINOTHIAZOLYL DERIVATIVES

[75] Inventors: Thomas H. Brown, Tewin; Graham J. Durant, Welwyn Garden City, both of England

[73] Assignee: Smith Kline & French Laboratories Limited, Welwyn Garden City, England

[21] Appl. No.: 120,807

[22] Filed: Feb. 12, 1980

[30] Foreign Application Priority Data

Feb. 21, 1979 [GB] United Kingdom ................. 7906070

[51] Int. Cl.³ ................. A61K 31/505; C07D 419/14; C07D 417/14
[52] U.S. Cl. .................... 514/272; 544/238; 544/295; 544/296; 544/311; 544/320; 544/231; 548/193
[58] Field of Search ............... 544/320, 321, 296, 295, 544/238; 424/251, 250

[56] References Cited

U.S. PATENT DOCUMENTS

| | | | |
|---|---|---|---|
| 3,932,644 | 1/1976 | Durant et al. | 424/251 |
| 3,980,781 | 9/1976 | Snell et al. | 424/251 |
| 4,145,546 | 3/1979 | Brown et al. | 544/321 |
| 4,154,834 | 5/1979 | Brown et al. | 544/320 |
| 4,159,329 | 6/1979 | Brown et al. | 544/321 |
| 4,165,377 | 8/1979 | Jones et al. | 424/270 |
| 4,165,378 | 8/1979 | Gilman et al. | 424/270 |
| 4,216,318 | 8/1980 | Brown et al. | 544/310 |

FOREIGN PATENT DOCUMENTS

| | | | |
|---|---|---|---|
| 0010894 | 5/1980 | European Pat. Off. | 544/320 |
| 1223686 | 3/1971 | United Kingdom . | |

Primary Examiner—Glennon H. Hollrah
Assistant Examiner—James H. Turnipseed
Attorney, Agent, or Firm—Joan S. Keps; Richard D. Foggio; Alan D. Lourie

[57] ABSTRACT

The compounds are guanidinothiazolyl derivatives which are histamine $H_2$-antagonists. A specific compound of the present invention is 2-[2-(2-guanidino-4-thiazolylmethylthio)ethylamino]-5-(6-methyl-3-pyridylmethyl)-4-pyrimidone.

8 Claims, No Drawings

GUANIDINOTHIAZOLYL DERIVATIVES

This invention relates to pharmacologically active compounds, to pharmaceutical compositions containing them and to methods of medical treatment using them.

Many pharmacologically active substances elicit their biological actions by interaction with specific sites known as receptors. Histamine is such a substance and has multiple biological actions. Those biological actions of histamine which are inhibited by drugs commonly called "antihistamines" (histamine $H_1$-antagonists), of which mepyramine, diphenhydramine and chlorpheniramine are typical examples, are mediated through histamine $H_1$-receptors. However, others of the biological actions of histamine are not inhibited by "antihistamines" (histamine $H_1$-antagonists) and actions of this type which are inhibited by burimamide are mediated through receptors which are termed histamine $H_2$-receptors. In this specification by histamine $H_2$-receptors is meant receptors defined by Black et al. (Nature, 236, 385 (1972)) as those histamine receptors which are not blocked by mepyramine but are blocked by burimamide. Compounds which block histamine $H_2$-receptors are referred to as histamine $H_2$-antagonists.

Blockade of histamine $H_2$-receptors is of value in inhibiting the biological actions of histamine which are not inhibited by "antihistamines" (histamine $H_1$-antagonists). Histamine $H_2$-antagonists are active, for example, as inhibitors of gastric acid secretion, as anti-inflammatory agents and as agents which act on the cardiovascular system, for example as inhibitors of the effects of histamine on blood pressure. Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockage of both types of receptors is useful. These conditions include inflammation mediated by histamine, for example skin inflammation, and those hypersensitivity responses due to the action of histamine at $H_1$- and $H_2$-receptors, for example allergies.

The compounds of the present invention are potent histamine $H_2$-antagonists.

The present invention provides compounds of Structure 1:

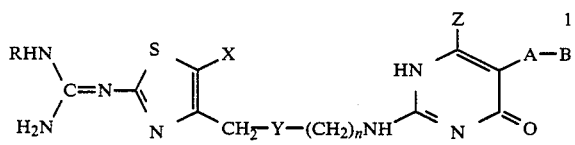

in which R is hydrogen, $C_1$–$C_6$ alkyl, $C_1$–$C_6$ alkanoyl or aroyl; X is hydrogen, chlorine, bromine or $C_1$–$C_6$ alkyl; Y is sulphur or methylene; n is 2 or 3; Z is hydrogen or lower alkyl; A is $C_1$–$C_5$ alkylene or —$(CH_2)_p W(CH_2)_q$— where W is oxygen or sulphur and p and q are such that their sum is from 1 to 4; and B is hydrogen, methyl, $C_3$–$C_6$ cycloalkyl, a heteroaryl group optionally substituted with lower alkyl, lower alkoxy, halo hydroxy or amino, or B is a naphthyl, 6-(2,3-dihydro-1,4-benzodioxinyl), or a 4- or 5-(1,3-benzodioxolyl) group, or a phenyl group optionally substituted with lower alkyl, lower alkoxy, halogen, aryl(lower alkoxy) (preferably benzyloxy), hydroxy, loweralkoxy-lower alkoxy, trifluoromethyl, di(lower alkyl)amino, phenoxy, halophenoxy, lower alkoxyphenoxy, phenyl, halophenyl or lower alkoxyphenyl; and pharmaceutically acceptable acid addition salts thereof.

The compounds of Structure 1 are shown and described as 4-pyrimidone derivatives and these derivatives exist in equilibrium with the corresponding 6-one tautomers. These compounds also exist to a lesser extent as the hydroxy tautomers, and the 2-amino pyrimidone group may also exist in 2-imino tautomeric forms.

Throughout this specification by the terms 'lower alkyl' and 'lower alkoxy' are meant alkyl and alkoxy groups which can be straight or branched and which contain 1 to 4 carbon atoms.

Specific examples of the group R are hydrogen, methyl, ethyl, acetyl, propionyl and benzoyl. Preferably R is hydrogen.

Specific examples of the group X are hydrogen, methyl and bromine. Preferably X is hydrogen.

Preferably Y is sulphur.

Preferably n is 2.

Specific examples of the group Z are hydrogen, methyl, ethyl and n-propyl. Preferably Z is hydrogen or methyl, particularly hydrogen.

Specific examples of the group A are methylene (—$CH_2$—), 1,2-ethanediyl (—$CH_2CH_2$—), 1,1-ethanediyl (—$CHCH_3$—), 1,4-butanediyl (—$CH_2CH_2CH_2CH_2$—), oxymethyl (—$OCH_2$—) and methoxymethyl (—$CH_2OCH_2$—). Preferably A is methylene.

Examples of B are the heteroaryl groups pyridyl, pyridyl N-oxide, furyl, thienyl, thiazolyl, oxazolyl, isothiazolyl, imidazolyl, pyrimidyl, pyrazinyl, pyridazyl, thiadiazolyl, quinolyl, isoquinolyl, 5,6,7,8-tetrahydroquinolyl, 1,3-dioxolopyridyl, benzimidazolyl and benzylthiazolyl. Particular meanings of B are the heteroaryl groups 2-furyl, 2-thienyl, 2-pyridyl, 3-pyridyl, 4-pyridyl, 2-thiazolyl, 2-imidazolyl, 2-pyrimidyl, 2-pyrazyl, 3-pyridazyl, 3-quinolyl and 1-isoquinolyl, which can be optionally substituted by one or more lower alkyl or lower alkoxy groups, and pyridyl substituted by hydroxy. Specific meanings of B are 3-pyridyl, 6-methyl-3-pyridyl, 5,6-dimethyl-3-pyridyl, 6-methoxy-3-pyridyl, 2-methoxy-4-pyridyl, 6-hydroxy-3-pyridyl, 2-hydroxy-4-pyridyl, 4-hydroxy-2-pyridyl and 5-(1,3-benzodioxolyl). Other specific meanings of B are 6-(2,3-dihydro-1,4-benzodioxinyl), 1-naphthyl, 2-naphthyl, 3-methoxyphenyl, 4-methoxyphenyl and 3,4-dimethoxyphenyl.

Preferably B is 3-pyridyl, 6-methyl-3-pyridyl or 2-hydroxy-4-pyridyl. Particularly preferably B is 6-methyl-3-pyridyl as we have found that compounds containing this group are approximately as active as the corresponding 3-pyridyl analogues but are less acutely toxic.

Four specific compounds of the invention are:

(a) 2-[2-(2-guanidino-4-thiazolylmethylthio)ethylamino]-5-(3-pyridylmethyl)-4-pyrimidone (b) 2-[2-(2-guanidino-4-thiazolylmethylthio)ethylamino]-5-(6-methyl-3-pyridylmethyl)-4-pyrimidone (c) 2-[2-(2-guanidino-4-thiazolylmethylthio)ethylamino]-5-(1,3-benzodioxolylmethyl)-4-pyrimidone (d) 2-[2-(2-guanidino-4-thiazolylmethylthio)ethylamino]-5-(2-hydroxy-4-pyridylmethyl)-4-pyrimidone and pharmaceutically acceptable acid-addition salts thereof.

Acid addition salts of the compounds of Structure 1 particularly comprise pharmaceutically-acceptable salts, for example acid-addition salts the compounds of Structure 1 form with hydrochloric, hydrobromic, sulphuric, phosphoric, acetic, citric and maleic acids. Such addition salts can conveniently be formed from the corresponding compounds of Structure 1 by standard procedures, for example by treating them with an acid in a lower alkanol or by the use of ion-exchange resins to form the required salt either directly from the compound in the base form or from a different addition salt.

The compounds of Structure 1 can be prepared by reacting an amine of Structure 2

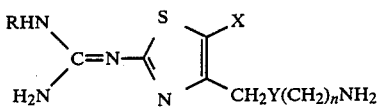
        2 where R, X, Y and n are as defined for Structure 1, with a pyrimidone of Structure 3

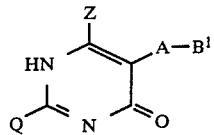
        3 where A and Z are as defined for Structure 1, $B^1$ has the same significance as B or is a protected derivative of B, Q is nitroamino ($NO_2NH-$), lower alkylthio, benzylthio, chlorine, bromine or other group which can be displaced with a primary amine, and subsequently removing any protecting groups present, and optionally converting the product into an acid-addition salt.

This process can be carried out in the absence of a solvent at an elevated temperature, e.g. when Q is methylthio at 150° C., or in the presence of a solvent, such as in refluxing pyridine. When Q is nitroamino this reaction is preferably carried out in a substantially inert solvent, for example refluxing ethanol or pyridine. Preferably Q is methylthio. Particularly preferably Q is nitroamino.

The compounds of Structure 1 in which Y is sulphur can also be prepared by (i) reacting a compound $GS(CH_2)_nNH_2$ where G is hydrogen or a thiol-protecting group, for example 4-methoxybenzyl, triphenylmethyl or $-S(CH_2)_nNH_2$ (in which the thiol is protected as the disulphide) and n is 2 or 3 with a pyrimidone of Structure 3, followed by removal of any thiol-protecting group present, and (ii) reacting the product with a compound of Structure 4

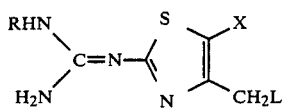
        4 where L is a group displaceable with a thiol, for example hydroxy, alkanoyloxy (preferably acetoxy), methanesulphonyloxy, benzenesulphonyloxy, p-toluenesulphonyloxy, lower alkoxy (preferably methoxy), chlorine, bromine or triarylphosphonium (preferably triphenylphosphonium), and removal of any protecting groups present, and optionally converting the product into an acid-addition salt. Preferably step (i) is carried out under conditions described above for the reaction with the amine of Structure 2. Preferably in step (ii) L is hydroxy or methoxy and the reaction is carried out under acidic conditions, for example in aqueous hydrochloric or hydrobromic acid.

The compounds of Structure 1 in which B is a heteroaryl group substituted by hydroxy, particularly 6-hydroxy-3-pyridyl or 2-hydroxy-4-pyridyl, can be prepared by dealkylating the corresponding compounds of Structure 1 in which B is a heteroaryl group substituted by lower alkoxy or benzyloxy, the alkyl and benzyl groups being used as protecting groups. Preferably such dealkylations are carried out using ethanolic hydrochloric or hydrobromic acid at an elevated temperature, for example the boiling point of the mixture.

The compounds of Structure 1 in which R is hydrogen can also be prepared from the corresponding compounds in which R is $C_1-C_6$-alkanoyl or aroyl by treatment with a dilute base, for example by warming with sodium hydroxide in aqueous ethanol.

The compounds of Structure 1 in which R is $C_1-C_6$-alkanoyl or aroyl can also be prepared from the corresponding compounds in which R is hydrogen by alkanoylation, e.g. acetylation with acetic anhydride, or aroylation, e.g. benzoylation with benzoic anhydride.

The amines of Structure 2 and the compounds of Structure 4 can be prepared by known methods and variations thereof, note Belgian Pat. No. 866,156 (Derwent Abstract 76288A).

The intermediates of Structure 3 in which Q is nitroamino can be prepared by reacting nitroguanidine with a compound of Structure 5

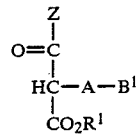
        5 in which $R^1$ is lower alkyl or aryl(lower alkyl), in the presence of a base. Preferably this reaction is carried out in a lower alkanol with a sodium lower alkoxide as the base at the boiling point of the reaction mixture.

The activity of the compounds of Structure 1 as histamine $H_2$-antagonists can be demonstrated by the inhibition of histamine-stimulated secretion of gastric acid from the lumen-perfused stomachs of rats anaesthetised with urethane, at doses of less than 16 micromoles per kilogram intravenously. This procedure is referred to in Ash and Schild, Brit. J. Pharmac. Chemother., 27, 247 (1966). For example the compounds of Examples 1 to 3 caused 50% inhibition of maximal acid secretion at doses of less than 0.1 micromole $kg^{-1}$.

Their activity as histamine $H_2$-antagonists can also be demonstrated by the inhibition of histamine-stimulated secretion of gastric acid from Heidenhain pouch dogs. For example the compounds of Examples 1 and 3 gave mean peak inhibition of over 50% at doses of 0.25 micromol $kg^{-1}$ i.v. and showed an extended duration of action.

Heidenhain pouch dogs are prepared by the following procedure. The abdomen of a male beagle (14–16 kg) is opened and the stomach is exteriorized. Blood vessels are ligated and cut at two places on the greater curvature to enable a piece of the fundus of the stomach to be cut away from the main stomach to form the pouch. The incision lines are sewn together to enable normal digestion. A stainless steel cannula is inserted into the pouch and the end not in the pouch is exteriorized through a stab wound in the abdominal wall to allow drainage of gastric juice under gravity. Finally, the abdomen is closed by a continuous suture. The dogs are ready for experimental use approximately three weeks after operation. The compounds of the invention are tested in Heidenhain pouch dogs by the following procedure. The dogs are starved for approximately 20 hours prior to the experiment and are then placed in Pavlov stands. A polythene cannula is placed in a leg vein and saline is infused for about one hour. A check is made that there is no basal acid secretion. Histamine (20 micromoles/hour) or pentagastrin (8 micrograms/kg/hour) is continuously infused in place of the saline. A plateau of acid secretion is reached after 1½ to 2 hours and the test compound is administered intravenously or orally (contained within a hard gelatin capsule). Gastric juice is collected by drainage under gravity into perspex tubes attached to the gastric cannula. Normally samples are collected over fifteen minute periods. The volumes of the samples are measured and aliquots are titrated to pH 7.4 with 0.1N sodium hydroxide. Acid secretion is expressed as the product of the volume and acid concentration.

Their activity as histamine $H_2$-antagonists can also be demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously they inhibit the vasodilator action of histamine. The potency of these compounds is illustrated by the effective dose producing 50% inhibition of gastric acid secretion in the anaesthetised rat and the dose producing 50% inhibition of the histamine-induced tachycardia in the isolated guinea pig atrium (less than $10^{-5}$ Molar).

The pharmaceutical compositions of the invention comprise a pharmaceutical carrier and a pharmacologically active compound of Structure 1 which can be in the base form or in the form of an addition salt with a pharmaceutically-acceptable acid.

The pharmaceutical carrier employed can be a solid or liquid. Examples of solid carriers are lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

For oral administration if a solid carrier is used, the composition can be prepared in the form of a tablet, capsule containing powder or pellets, troche or lozenge. The amount of solid carrier in a unit dosage form will generally be from about 25 mg to about 300 mg; if a liquid carrier is used, the composition can be in the form of a syrup, emulsion, multiple emulsion, sterile injectable liquid or an aqueous or non-aqueous solution or liquid suspension. Other additives such as preservatives, for example antioxidants or antibacterials, and/or flavouring or colouring agents can also be included. The sterile liquids can be prepared in ampoules, multidose vials or unit dose disposable systems. For topical application the preparation can be in a semi-solid form, for example a cream, paste, ointment or gel, in a liquid or aerosol form. The composition can also be a suppository formulation. The pharmaceutical compositions are prepared by conventional techniques involving procedures such as milling, mixing, granulating and compressing, spray drying, freeze drying or dissolving or dispersing the ingredients as appropriate to the desired preparation. The active ingredient is present in the compositions in an effective amount to block histamine $H_2$-receptors. Preferably, each dosage unit contains the active ingredient in an amount of from about 50 mg to about 250 mg.

The pharmaceutical compositions can also comprise an accepted drug in addition to a compound of Structure 1, for example a histamine $H_1$-antagonist, e.g. mepyramine.

A method of blocking histamine $H_2$-receptors by administering to an animal a compound of Structure 1 is also an object of this invention.

The active ingredient is preferably administered one to six times per day. The daily dosage regimen is preferably from about 150 mg to about 1500 mg. The route of administration can be oral, parenteral, topical or rectal.

This invention is illustrated but in no way limited by the following Examples, where all temperatures are in degrees Centigrade:

EXAMPLE 1

(i) Sodium (1.15 g) was dissolved in methanol (50 ml), and nitroguanidine (4.7 g) was added to the cooled solution. The mixture was heated under reflux for 45 minutes, ethyl 2-formyl-3-(3-pyridyl)propionate (9.3 g) was added portionwise and the mixture was heated under reflux for 45 hours and evaporated to dryness. Water was added to the residue and the mixture was extracted with chloroform. The aqueous phase was adjusted to pH 5 with acetic acid, and the solid which was precipitated was filtered off, washed and dried to give 2-nitroamino-5-(3-pyridylmethyl)-4-pyrimidone, m.p. 214.5°–216°, in 38% yield.

(ii) Sodium ethoxide (prepared from 0.23 g sodium) in dry ethanol (20 ml) was added to a stirred suspension of 2-(2-guanidino-4-thiazolylmethylthio)ethylamine dihydrochloride (1.5 g) in dry ethanol (25 ml). The mixture was stirred for 0.5 hour and sodium chloride was filtered off. 2-Nitroamino-5-(3-pyridylmethyl)-4-pyrimidone (0.99 g) was added to the filtrate and the mixture was boiled under reflux for 20 hours, evaporated to dryness and the residual oil was heated at 100° for 8 hours to give 2-[2-(2-guanidino-4-thiazolylmethylthio)ethylamino]-5-(3-pyridylmethyl)-4-pyrimidone as a crude oil. This oil was dissolved in ethanol, hydrogen chloride in ethanol and ether were added and the solid which precipitated out was recrystallised from ethanol/2-propanol to give the trihydrochloride (0.73 g) m.p. 219°–222°.

EXAMPLE 2

(i) A solution of ethyl 2-formyl-3-(5-(1,3-benzodioxolyl)propionate (7.5 g) in methanol (20 ml) was added to sodium methoxide in methanol (prepared from 0.689 g sodium and 50 ml methanol). Nitroguanidine (3.12 g) was added to this stirred mixture and the mixture was heated under reflux for 18 hours and evaporated. The residue was dissolved in water (200 ml) and the solution was extracted with chloroform. The aqueous phase was adjusted to pH 5 with acetic acid and the white solid which precipitated out was filtered off to give 2-nitroamino-5-(5-(1,3-benzodioxolyl)methyl)-4-pyrimidone (4.08 g) m.p. 200°–202°. A sample recrystallised from aqueous acetic acid had m.p. 201.5°–202.5°.

(ii) A solution of sodium ethoxide (prepared from 0.23 g sodium) in ethanol (20 ml) was added to a solution of 2-(2-guanidino-4-thiazolylmethylthio)ethylamine dihydrochloride (1.5 g) in ethanol and the mixture was stirred for 0.5 hour, filtered to remove sodium chloride and evaporated to dryness. 2-Nitroamino-5-(5-(1,3-benzodioxolyl)methyl)-4-pyrimidone (1.16 g) and pyridine (20 ml) were added to the residue and the mixture was boiled under reflux for 16 hours and evaporated to give 2-[2-(2-guanidino-4-thiazolylmethylthio)ethylamino]-5-(5-(1,3-benzodioxolyl)methyl)-4-pyrimidone. This residue was treated with dilute HCl in 2-propanol, the mixture was evaporated to dryness and the residue was recrystallised from methanol-ether to give 2-[2-(2-guanidino-4-thiazolylmethylthio)ethylamino]-5-(5-(1,3-benzodioxolyl)methyl)-4-pyrimidone dihydrochloride (0.53 g) m.p. 207°–212° (decomp). Treatment of the free base with sulphuric acid in aqueous 2-propanol gives the corresponding sulphate.

EXAMPLE 3

(a)(i) A mixture of 6-methylpyridine-3-carboxaldehyde (51.57 g), malonic acid (44.30 g), piperidine (6 ml) and pyridine (300 ml) was stirred at 100° for 3 hours and was allowed to cool. The mixture was evaporated to dryness, water was added to the residue and the solid which separated out was filtered off and recrystallised from ethanol-acetic acid to give 3-(6-methyl-3-pyridyl)acrylic acid (41.25 g) m.p. 213.5°–215.5°.

(ii) A stirred mixture of 3-(6-methyl-3-pyridyl)acrylic acid (50.70 g), dry ethanol (350 ml) and concentrated sulphuric acid (25 ml) was heated under reflux for 18 hours and ethanol (~250 ml) was removed by evaporation. The residue was poured into ice-aqueous ammonia and the mixture was extracted with ether. The ether extracts were washed with water and evaporated to an oil which crystallised on standing to give ethyl 3-(6-methyl-3-pyridyl)acrylate m.p. 36°–37°.

(iii) Ethyl 3-(6-methyl-3-pyridyl)acrylate (60.36 g) was hydrogenated in ethanol at 35° and 355 kPa using palladium-on-charcoal catalyst (10%, 1.0 g). The mixture was filtered and the filtrate was evaporated to give ethyl 3-(6-methyl-3-pyridyl)propionate as an oil.

(iv) Ethyl 3-(6-methyl-3-pyridyl)propionate 57.79 g) and ethyl formate (23.71 g) were added over 2.5 hours to a stirred mixture of sodium wire (6.88 g) and ether (200 ml) cooled in an ice-salt bath. The mixture was stirred for 20 hours and the ether was removed by evaporation. Thiourea (22.76 g) and ethanol (175 ml) were added to the residue and the mixture was heated under reflux for 7 hours and evaporated to dryness. Water (200 ml) was added to the residue and the mixture was adjusted to pH 6 with acetic acid. The solid was filtered off and recrystallised from methanol/acetic acid to give 5-(6-methyl-3-pyridylmethyl)-2-thiouracil (17.24 g) m.p. 240°–241°.

(v) Methyl iodide (13.79 g) was added to a stirred solution of 5-(6-methyl-3-pyridylmethyl)-2-thiouracil (22.66 g) and sodium hydroxide (8.0 g) in water (250 ml), and the mixture was heated at 70° for 1 hour and stirred at room temperature overnight. Acetic acid was added until pH 5 and the mixture was evaporated to a volume of 50 ml. The solid was filtered off and was recrystallised from ethanol-acetic acid to give 5-(6-methyl-3-pyridylmethyl)-2-methylthio-4-pyrimidone (10.16 g) m.p. 197°–197.5°.

(vi) Equimolar amounts of 5-(6-methyl-3-pyridylmethyl)-2-methylthio-4-pyrimidone and 2-(2-guanidino-4-thiazolylmethylthio)ethylamine are refluxed together with pyridine for 48 hours to give 2-[2-(2-guanidino-4-thiazolylmethylthio)ethylamino]-5-(6-methyl-3-pyridylmethyl)-4-pyrimidone.

(b)(i) Ethyl 3-(6-methyl-3-pyridyl)propionate was formylated with ethyl formate and sodium hydride in 1,2-dimethoxyethane to give ethyl 2-formyl-3-(6-methyl-3-pyridyl)propionate m.p. 142°–144°.

(ii) A solution of ethyl 2-formyl-3-(6-methyl-3-pyridyl)propionate (1.55 g) in methanol (20 ml) was added to a solution of sodium methoxide (from 0.161 g sodium) in methanol (20 ml). Dried nitroguanidine (0.729 g) was added over 5 minutes and the mixture was stirred and boiled under reflux overnight and evaporated to dryness. The residue was dissolved in water (50 ml) and the solution was extracted with chloroform (2×25 ml, subsequently discarded) and acidified to pH 5 with acetic acid. The solid which precipitated out was filtered off and recrystallised from methanol-acetic acid to give 2-nitroamino-5-(6-methyl-3-pyridylmethyl)-4-pyrimidone (0.5 g) m.p. 215°–216° (decomp.).

(iii) 2-Nitroamino-5-(6-methyl-3-pyridylmethyl)-4-pyrimidone (5.21 g) and 2-(2-guanidino-4-thiazolylmethylthio)ethylamine (2.98 g) were heated under reflux in dry pyridine for 9 hours. The mixture was evaporated and the residue was washed with water to give 2-[2-(2-guanidino-4-thiazolylmethylthio)ethylamino]-5-(6-methyl-3-pyridylmethyl)-4-pyrimidone which was treated with hydrogen chloride in ethanol-ether to give the trihydrochloride (0.92 g). This was converted into the free base by dissolving the material in water, adjusting the mixture to pH 9 with sodium bicarbonate, and extracting the mixture with chloroform and evaporating the extracts to dryness. A sample of the free base recrystallised from aqueous 2-propanol had m.p. 161°–164°.

EXAMPLE 4

2-(2-Guanidino-4-thiazolylmethylthio)ethylamine is heated under reflux in pyridine for 12 hours with 0.75 molar equivalents of:
(a) 2-nitroamino-5-(2-methoxy-4-pyridylmethyl)-4-pyrimidone
(b) 2-nitroamino-5-(6-methoxy-3-pyridylmethyl)-4-pyrimidone
and the mixture is heated under reflux in pyridine for 12 hours to give:
(a) 2-[2-(2-guanidino-4-thiazolylmethylthio)ethylamino]-5-(2-methoxy-4-pyridylmethyl)-4-pyrimidone
(b) 2-[2-(2-guanidino-4-thiazolylmethylthio)ethylamino]-5-(6-methoxy-3-pyridylmethyl)-4-pyrimidone.

When the purified products are boiled under reflux in 2N hydrogen chloride in ethanol trihydrochlorides of the following compounds are prepared:
(c) 2-[2-(2-guanidino-4-thiazolylmethylthio)ethylamino]-5-(2-hydroxy-4-pyridylmethyl)-4-pyrimidone
(d) 2-[2-(2-guanidino-4-thiazolylmethylthio)ethylamino]-5-(6-hydroxy-3-pyridylmethyl)-4-pyrimidone The methoxy compounds can also be demethylated using boron tribromide in dichloromethane.

EXAMPLE 5

2-(2-Guanidino-4-thiazolylmethylthio)ethylamine is heated under reflux in pyridine for 12 hours with 0.75 molar equivalents of 2-nitroamino-5-(4-methoxy-2-pyridylmethyl)-4-pyrimidone to give 2-[2-(2-guanidino-4-thiazolylmethylthio)ethylamino]-5-(4-methoxy-2-pyridylmethyl)-4-pyrimidone. When this product is boiled under reflux in 2N hydrogen bromide in ethanol 2-[2-(2-guanidino-4-thiazolylmethylthio)ethylamino]-5-(4-hydroxy-2-pyridylmethyl)-4-pyrimidone trihydrobromide is produced.

EXAMPLE 6

2-(2-Guanidino-4-thiazolylmethylthio)ethylamine is heated under reflux in pyridine for 12 hours with 1.5 molar equivalents of 2-nitroamino-5-(5,6-dimethyl-3-pyridylmethyl)-4-pyrimidone to give 2-[2-(2-guanidino-4-thiazolylmethylthio)ethylamino]-5-(5,6-dimethyl-3-pyridylmethyl)-4-pyrimidone.

EXAMPLE 7

2-Guanidino-4-chloromethylthiazole hydrochloride is reacted with 2-(2-mercaptoethylamino)-5-(6-methyl-3-pyridylmethyl)-4-pyrimidone and sodium ethoxide in ethanol to give 2-[2-(2-guanidino-4-thiazolylmethylthio)ethylamino]-5-(6-methyl-3-pyridylmethyl)-4-pyrimidone.

EXAMPLE 8

2-(2-Guanidino-4-thiazolylmethylthio)ethylamine is heated under reflux in pyridine for 12 hours with 0.75 molar equivalents of:
(a) 2-nitroamino-5-(2-furylmethyl)-4-pyrimidone
(b) 2-nitroamino-5-(3-methoxybenzyl)-4-pyrimidone
(c) 2-nitroamino-5-(3,4,5-trimethoxybenzyl)-4-pyrimidone
(d) 2-nitroamino-5-[6-(2,3-dihydro-1,4-benzodioxinyl)methyl]-4-pyrimidone
(e) 2-nitroamino-5-(1-naphthylmethyl)-4-pyrimidone
to give:

(a) 2-[2-(2-guanidino-4-thiazolylmethylthio)ethylamino]-5-(2-furylmethyl)-4-pyrimidone
(b) 2-[2-(2-guanidino-4-thiazolylmethylthio)ethylamino]-5-(3-methoxybenzyl)-4-pyrimidone
(c) 2-[2-(2-guanidino-4-thiazolylmethylthio)ethylamino]-5-(3,4,5-trimethoxybenzyl)-4-pyrimidone
(d) 2-[2-(2-guanidino-4-thiazolylmethylthio)ethylamino]-5-(6-(2,3-dihydro-1,4-benzodioxinyl)methyl]-4-pyrimidone
(e) 2-[2-(2-guanidino-4-thiazolylmethylthio)ethylamino]-5-(1-naphthylmethyl)-4-pyrimidone

EXAMPLE 9

2-(2-Guanidino-4-thiazolylmethylthio)ethylamine is heated under reflux in pyridine for 12 hours with 0.75 molar equivalents of:
(a) 2-nitroamino-5-(N-oxo-3-pyridylmethyl)-4-pyrimidone
(b) 2-nitroamino-5-(N-oxo-6-methyl-3-pyridylmethyl)-4-pyrimidone
to give:
(a) 2-[2-(2-guanidino-4-thiazolylmethylthio)ethylamino]-5-(N-oxo-3-pyridylmethyl)-4-pyrimidone
(b) 2-[2-(2-guanidino-4-thiazolylmethylthio)ethylamino]-5-(N-oxo-6-methyl-3-pyridylmethyl)-4-pyrimidone The starting materials can be prepared by oxidation of intermediates described in Examples 1 and 3 with 3-chloroperoxybenzoic acid in acetic acid.

EXAMPLE 10

2-(2-Guanidino-4-thiazolylmethylthio)ethylamine and an equimolar amount of
(a) 5-(2-pyridylmethyl)-2-methylthio-4-pyrimidone
(b) 5-(4-pyridylmethyl)-2-methylthio-4-pyrimidone
(c) 5-(2-thiazolylmethyl)-2-methylthio-4-pyrimidone
(d) 5-(3-quinolylmethyl)-2-methylthio-4-pyrimidone
(e) 5-(2-thienylmethyl)-2-methylthio-4-pyrimidone
(f) 5-(5-methylbenzyl)-2-methylthio-4-pyrimidone
(g) 5-(4-chlorobenzyl)-2-methylthio-4-pyrimidone
(h) 5-(3-chlorobenzyl)-2-methylthio-4-pyrimidone
(i) 5-(3,4-dichlorobenzyl)-2-methylthio-4-pyrimidone
are heated at 160°–170° for 6 hours to give:

(a) 2-[2-(2-guanidino-4-thiazolylmethylthio)ethylamino]-5-(2-pyridylmethyl)-4-pyrimidone
(b) 2-[2-(2-guanidino-4-thiazolylmethylthio)ethylamino]-5-(4-pyridylmethyl)-4-pyrimidone
(c) 2-[2-(2-guanidino-4-thiazolylmethylthio)ethylamino]-5-(2-thiazolylmethyl)-4-pyrimidone
(d) 2-[2-(2-guanidino-4-thiazolylmethylthio)ethylamino]-5-(3-quinolylmethyl)-4-pyrimidone
(e) 2-[2-(2-guanidino-4-thiazolylmethylthio)ethylamino]-5-(2-thienylmethyl)-4-pyrimidone
(f) 2-[2-(2-guanidino-4-thiazolylmethylthio)ethylamino]-5-(4-methylbenzyl)-4-pyrimidone
(g) 2-[2-(2-guanidino-4-thiazolylmethylthio)ethylamino]-5-(4-chlorobenzyl)-4-pyrimidone
(h) 2-[2-(2-guanidino-4-thiazolylmethylthio)ethylamino]-5-(3-chlorobenzyl)-4-pyrimidone
(i) 2-[2-(2-guanidino-4-thiazolylmethylthio)ethylamino]-5-(3,4-dichlorobenzyl)-4-pyrimidone.

EXAMPLE 11

2-(2-Guanidino-4-thiazolylmethylthio)ethylamine and an equimolar amount of:

(a) 2-methylthio-5-methyl-4-pyrimidone
(b) 2-methylthio-5-hexyl-4-pyrimidone
(c) 5-cyclohexylmethyl-2-methylthio-4-pyrimidone
are heated at 160°–170° for 6 hours to give:

(a) 2-[2-(2-guanidino-4-thiazolylmethylthio)ethylamino]-5-methyl-4-pyrimidone
(b) 2-[2-(2-guanidino-4-thiazolylmethylthio)ethylamino]-5-hexyl-4-pyrimidone
(c) 2-[2-(2-guanidino-4-thiazolylmethylthio)ethylamino]-5-cyclohexylmethyl-4-pyrimidone

EXAMPLE 12

Equimolar amounts of:
(a) 4-(2-guanidino-4-thiazolyl)butylamine
(b) 5-(2-guanidino-4-thiazolyl)pentylamine
(c) 2-(2-methylguanidino-4-thiazolylmethylthio)ethylamine
(d) 2-(2-acetylguanidino-4-thiazolylmethylthio)ethylamine
and 2-nitroamino-5-(6-methyl-3-pyridylmethyl)-4-pyrimidone are refluxed together in ethanol for 24 hours to give:

(a) 2-[4-(2-guanidino-4-thiazolyl)butylamino]-5-(6-methyl-3-pyridylmethyl)-4-pyrimidone
(b) 2-[5-(2-guanidino-4-thiazolyl]pentylamino]-5-(6-methyl-3-pyridylmethyl)-4-pyrimidone
(c) 2-[2-(2-methylguanidino-4-thiazolylmethylthio)ethylamino]-5-(6-methyl-3-pyridylmethyl)-4-pyrimidone
(d) 2-[2-(2-acetylguanidino-4-thiazolylmethylthio)ethylamino]-5-(6-methyl-3-pyridylmethyl)-4-pyrimidone.

EXAMPLE 13

Equimolar amounts of:
(a) 4-(2-methylguanidino-4-thiazolyl)butylamine (preparable by heating 2-(2-methylguanidino)-4-(4-phthalimidobutyl)thiazole hydrobromide in aqueous ethanol with sodium hydroxide at pH 12 for 15 minutes).
(b) 4-(2-guanidino-5-methyl-4-thiazolyl)butylamine
(c) 4-(2-guanidino-5-bromo-4-thiazolyl)butylamine
(d) 3-(2-guanidino-4-thiazolylmethylthio)propylamine
(e) 2-(2-n-butylguanidino-4-thiazolylmethylthio)ethylamine and 2-nitroamino-5-(6-methyl-3-pyridylmethyl)-4-pyrimidone are heated under reflux in pyridine for 9 hours to give (a) 2-[4-(2-methylguanidino-4-thiazolyl)butylamino]-5-(6-methyl-3-pyridylmethyl)-4-pyrimidone
(b) 2-[4-(2-guanidino-5-methyl-4-thiazolyl)butylamino]-5-(6-methyl-3-pyridylmethyl)-4-pyrimidone
(c) 2-[4-(2-guanidino-5-bromo-4-thiazolyl)butylamino]-5-(6-methyl-3-pyridylmethyl)-4-pyrimidone
(d) 2-[3-(2-guanidino-4-thiazolylmethylthio)propylamino]-5-(6-methyl-3-pyridylmethyl)-4-pyrimidone
(e) 2-[2-(2-n-butylguanidino-4-thiazolylmethylthio)ethylamino]-5-(6-methyl-3-pyridylmethyl)-4-pyrimidone.

EXAMPLE 14

A pharmaceutical composition for oral administration is prepared containing

|   |   | % w/w |
|---|---|---|
| A | 2-[2-(2-guanidino-4-thiazolylmethylthio)ethylamino]-5-(6-methyl-3-pyridylmethyl)-4-pyrimedome | 55 |
|   | Dibasic calcium phosphate dihydrate | 20 |
|   | Approved colouring agent | 0.5 |
|   | Polyvinlypyrrolidone | 4.0 |
| B | Microcrystalline cellulose | 8.0 |
|   | Maize starch | 8.0 |
|   | Sodium starch glycollate | 4.0 |
|   | Magnesium stearate | 0.5 | by mixing together the ingredients A (substituting lactose or microcrystalline cellulose for dibasic calcium phosphate dihydrate if desired), adding a concentrated solution of polyvinylpyrrolidone, and granulating, drying and screening the dried granules; adding the ingredients B to the dried granules and compressing the mixture into tablets, containing 100, 150 or 200 mg of active ingredient.

Other compounds of the invention, for example those specifically described in Examples 1, 2 and 4 to 6 and 8 to 13 can be formulated into pharmaceutical compositions by a similar procedure.

EXAMPLE 15

An injectable pharmaceutical composition is prepared by dissolving 2-[2-(2-guanidino-4-thiazolylmethylthio)ethylamino]-5-(3-pyridylmethyl)-4-pyrimidone trihydrochloride in sterile water to give a 5% w/w solution. The solution is clarified by filtration and filled into vials which are sealed and sterilised. A suitable vial contains 2 ml of the solution.

EXAMPLE 16

Reaction of 2-[2-(2-guanidino-4-thiazolylmethylthio)ethylamino]-5-(6-methyl-3-pyridylmethyl)-4-pyrimidone with acetic anhydride or benzoic anhydride in pyridine gives 2-[2-(2-acetylguanidino-4-thiazolylmethylthio)ethylamino]-5-(6-methyl-3-pyridylmethyl)-4-pyrimidone and 2-[2-(2-benzoylguanidino-4-thiazolylmethylthio)ethylamino]-5-(6-methyl-3-pyridylmethyl)-4-pyrimidone.

EXAMPLE 17

Reaction of (a) 5-benzyloxy-2-methylthio-4-pyrimidone
(b) 5-(2-(4-methoxybenzyloxy)ethyl)-2-methylthio-4-pyrimidone
(c) 5-(2-(4-methoxybenzylthio)ethyl)-2-methylthio-4-pyrimidone
(d) 5-(2-(3-pyridylmethylthio)ethyl)-2-methylthio-4-pyrimidone
(e) 5-(2-phenylethyl)-2-methylthio-4-pyrimidone
(f) 5-(2-phenylethyl)-6-methyl-2-methylthio-4-pyrimidone
(g) 5-(4-phenylbutyl)-2-methylthio-4-pyrimidone with one equivalent of 2-(2-guanidino-4-thiazolylmethylthio)ethylamine under reflux in pyridine for 24 hours gives (a) 2-[2-(2-guanidino-4-thiazolylmethylthio)ethylamino]-5-benzyloxy-4-pyrimidone
(b) 2-[2-(2-guanidino-4-thiazolylmethylthio)ethylamino]-5-(2-(4-methoxybenzyloxy)ethyl)-4-pyrimidone
(c) 2-[2-(2-guanidino-4-thiazolylmethylthio)ethylamino]-5-(2-(4-methoxybenzylthio)ethyl)-4-pyrimidone
(d) 2-[2-(2-guanidino-4-thiazolylmethylthio)ethylamino]-5-(2-(3-pyridylmethylthio)ethyl)-4-pyrimidone
(e) 2-[2-(2-guanidino-4-thiazolylmethylthio)ethylamino]-5-(2-phenylethyl)-4-pyrimidone
(f) 2-[2-(2-guanidino-4-thiazolylmethylthio)ethylamino]-5-(2-phenylethyl)-6-methyl-4-pyrimidone
(g) 2-[2-(2-guanidino-4-thiazolylmethylthio)ethylamino]-5-(4-phenylbutyl)-4-pyrimidone

EXAMPLE 18

Substitution of the following 3-(heteroaryl)propionates:
(a) ethyl 3-(2-methoxy-3-pyridyl)propionate
(b) ethyl 3-(4,6-dimethoxy-3-pyridyl)propionate
(c) ethyl 3-(2,6-dimethoxy-4-pyridyl)propionate
(d) ethyl 3-(4,5-dimethoxy-2-pyridyl)propionate
(e) ethyl 3-(5-hydroxy-2-pyridyl)propionate
(f) ethyl 3-(4-hydroxy-2-pyrimidyl)propionate
(g) ethyl 3-(4-hydroxy-5-methoxy-2-pyridyl)propionate
(h) ethyl 3-(4-hydroxy-3-methoxy-2-pyridyl)propionate (i) ethyl 3-(4,5-dimethyl-2-thienyl)propionate
(j) ethyl 3-(6-amino-3-pyridyl)propionate
(k) ethyl 3-(4-isoquinolyl)propionate
(l) ethyl 3-(3-chloro-2-pyridyl)propionate
for ethyl 3-(6-methyl-3-pyridyl)propionate in the procedure of Example 3 b(i)–(ii) gives the corresponding 2-nitroamino-4-pyrimidones which are heated under reflux in pyridine with 2-(2-guanidino-4-thiazolylmethylthio)ethylamine to give the corresponding 2-[2-(2-guanidino-4-thiazolylmethylthio)ethylamino]-5-(heteroarylmethyl)-4-pyrimidones.

The starting materials may be prepared by condensing the corresponding heterocyclic carboxaldehyde with (i) malonic acid, and hydrogenating and esterifying the products or (ii) diethyl malonate, reducing the product with sodium borohydride followed by hydrolysis, monodecarboxylation and esterification, or by reacting a halomethylheterocyclic derivative with sodium and diethyl malonate, and hydrolysing, monodecarboxylating and esterifying the product.

EXAMPLE 19

Substitution of the following 3-arylpropionates:
(a) ethyl 3-(3-benzyloxyphenyl)propionate
(b) ethyl 3-(3-methoxyethoxymethoxyphenyl)propionate (prepared by reacting ethyl 3-(3-hydroxyphenyl)propionate with 2-methoxyethoxymethyl chloride)
(c) ethyl 3-(3-trifluoromethylphenyl)propionate
(d) ethyl 3-(4-dimethylaminophenyl)propionate
(e) ethyl 3-(4-phenoxyphenyl)propionate
(f) ethyl 3-(4-(4-chlorophenoxy)phenyl)propionate
(g) ethyl 3-(4-(4-methoxyphenoxy)phenyl)propionate
(h) ethyl 3-(4-biphenylyl)propionate
(i) ethyl 3-(4'-chloro-4-biphenylyl)propionate
(j) ethyl 3-(4'-methoxy-4-biphenylyl)propionate
for ethyl 3-(6-methyl-3-pyridyl)propionate in the procedure of Example 3(b) gives the corresponding 2-[2-(2-guanidino-4-thiazolylmethylthio)ethylamino]-5-(arylmethyl)-4-pyrimidones.

Treatment of the product from (b) with hydrochloric acid gives the 5-(3-hydroxybenzyl)pyrimidone.

EXAMPLE 20

Substitution of the following 3-(heteroaryl)propionates:
(a) ethyl 3-(2-thiazolyl)propionate
(b) ethyl 3-(5-oxazolyl)propionate
(c) ethyl 3-(3-isothiazolyl)propionate
(d) ethyl 3-(2-pyrimidyl)propionate
(e) ethyl 3-(5-pyrimidyl)propionate
(f) ethyl 3-(2-pyrazyl)propionate
(g) ethyl 3-(4-pyridazyl)propionate
(h) ethyl 3-(2-(5-amino-1,3,4-thiadiazolyl)propionate
(i) ethyl 3-(1-isoquinolyl)propionate
(j) ethyl 3-(2-benzimidazolyl)propionate
(k) ethyl 3-(2-benzthiazolyl)propionate for ethyl 3-(6-methyl-3-pyridyl)propionate in the procedure of Example 3(b) gives the corresponding 2-[2-(2-guanidino-4-thiazolylmethylthio)ethylamino]-5-(heteroarylmethyl)-4-pyrimidones.

The starting materials can be prepared as described in Example 18.

EXAMPLE 21

Substitution of 3-[1-(4-methoxybenzyl)imidazol-2-yl]-acrylic acid for 3-(6-methyl-3-pyridyl)acrylic acid in the procedure of Example 3(a) (ii)–(vi) and deprotection of the product with anisole and hydrogen bromide in acetic acid gives 2-[2-(2-guanidino-4-thiazolylmethylthio)ethylamino]-5-(2-imidazolylmethyl)-4-pyrimidone trihydrobromide.

What is claimed is:

1. A compound of the formula

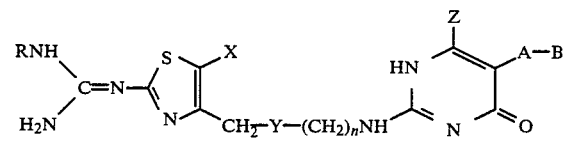

in which R is hydrogen, $C_1$–$C_6$ alkyl, $C_1$–$C_6$ alkanoyl or benzoyl; X is hydrogen, chlorine, bromine or $C_1$–$C_6$ alkyl; Y is sulphur or methylene; n is 2 or 3; Z is hydrogen or lower alkyl; A is $C_1$–$C_5$ alkylene or —$(CH_2)_p W(CH_2)_q$— where W is oxygen or sulphur and p and q are such that their sum is from 1 to 4; B is heteroaryl selected from imidazolyl, pyrimidyl, pyrazinyl, pyridazyl, 5-amino-1,3,4-thiadiazolyl, 1,3-dioxolopyridyl and benzimidazolyl, or B is 6-(2,3-dihydro-1,4-benzodioxinyl), or 4- or 5-(1,3-benzodioxolyl); and pharmaceutically acceptable acid addition salts thereof.

2. A compound of claim 1 in which R is hydrogen and X is hydrogen.

3. A compound according to claim 1 in which Y is sulphur, n is 2 and Z is hydrogen.

4. A compound according to any one of claims 1, 2 or 3 in which A is methylene.

5. A compound according to any one of claims 1, 2 or 3 in which B is 5-(1,3-benzodioxolyl).

6. A compound of claim 1, said compound being 2-[2-(2-guanidino-4-thiazolylmethylthio)ethylamino]-5-(5-(1,3-benzodioxolyl)methyl)-4-pyrimidone or a pharmaceutically acceptable acid addition salt thereof.

7. A pharmaceutical composition having histamine $H_2$-receptor blocking activity comprising in an effective amount to block said receptors a pharmacologically-active compound of claim 1 and a pharmaceutically acceptable diluent or carrier.

8. A method of blocking histamine $H_2$-receptors which comprises administering to an animal in need thereof in an effective amount to block said receptors a compound of claim 1.

* * * * *